(12) United States Patent
Takamatsu et al.

(10) Patent No.: US 7,893,311 B2
(45) Date of Patent: *Feb. 22, 2011

(54) METHOD FOR PRODUCING ETHYLENE AND PROPYLENE

(75) Inventors: Yoshikazu Takamatsu, Tokyo (JP); Kouji Nomura, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 393 days.

This patent is subject to a terminal disclaimer.

(21) Appl. No.: 12/067,037

(22) PCT Filed: Sep. 14, 2006

(86) PCT No.: PCT/JP2006/318297

§ 371 (c)(1), (2), (4) Date: Mar. 14, 2008

(87) PCT Pub. No.: WO2007/032448

PCT Pub. Date: Mar. 22, 2007

(65) Prior Publication Data

US 2010/0063340 A1 Mar. 11, 2010

(30) Foreign Application Priority Data

Sep. 16, 2005 (JP) .......................... P2005-270323

(51) Int. Cl.
*C07C 4/06* (2006.01)
(52) U.S. Cl. ..................... 585/651; 585/653; 208/73; 208/76; 208/113
(58) Field of Classification Search ................. 585/651, 585/653; 208/73, 76, 120.15, 113; 502/64, 502/71, 77
See application file for complete search history.

(56) References Cited

U.S. PATENT DOCUMENTS

| 4,527,001 | A | 7/1985 | Kaiser |
| 4,613,721 | A | 9/1986 | Kaiser |
| 5,043,522 | A | 8/1991 | Leyshon et al. |
| 5,171,921 | A | 12/1992 | Gaffney et al. |
| 6,307,117 | B1 | 10/2001 | Tsunoda et al. |
| 6,977,321 | B1 | 12/2005 | Dath et al. |
| 2003/0062291 | A1 | 4/2003 | Dath et al. |

FOREIGN PATENT DOCUMENTS

| JP | 49-41322 A | 4/1974 |
| JP | 50-49233 A | 5/1975 |
| JP | 3-27327 A | 2/1991 |
| JP | 6-73382 A | 3/1994 |
| JP | 06-299166 A | 10/1994 |
| JP | 06-330055 A | 11/1994 |
| JP | 11-246445 A | 9/1999 |
| WO | WO-96/13331 A1 | 5/1996 |
| WO | WO-00/10948 A1 | 3/2000 |
| WO | WO-2004/072002 A1 | 8/2004 |
| WO | WO-2006/009099 A1 | 1/2006 |

*Primary Examiner*—Tam M Nguyen
(74) *Attorney, Agent, or Firm*—Birch, Stewart, Kolasch & Birch, LLP

(57) ABSTRACT

The invention is to provide a catalyst excellent in product producibility and selectivity, and in coking degradation resistance and regeneration degradation resistance, which is for production of ethylene and propylene through catalytic conversion from a hydrocarbon material. The invention relates to a method for producing ethylene and propylene through catalytic conversion from an olefin, by contacting a hydrocarbon material with a zeolite-containing shaped catalyst satisfying the following requirements (1) to (6), in a reactor:

(1) the zeolite is an intermediate pore-size zeolite having a pore size of from 5 to 6.5 angstroms,
(2) the zeolite does not substantially contain a proton,
(3) the zeolite contains at least one metal selected from the group consisting of metals belonging to the Group IB of the Periodic Table,
(4) the zeolite-containing shaped catalyst comprises silica as a binder,
(5) the zeolite-containing shaped catalyst has a side-crush strength of at least 2.5 N/mm,
(6) the zeolite-containing shaped catalyst has a sodium content of 500 ppm or less as an H-exchange type thereof.

10 Claims, No Drawings

METHOD FOR PRODUCING ETHYLENE AND PROPYLENE

TECHNICAL FIELD

The present invention relates to a method for producing ethylene and propylene through catalytic conversion from a hydrocarbon material. More precisely, the invention relates to a method for producing ethylene and propylene from a hydrocarbon material by bringing it contact with a zeolite-containing shaped catalyst in a fixed-bed reactor to thereby carry out catalytic conversion.

BACKGROUND ART

Many methods are known for catalytic conversion from an olefin-containing hydrocarbon material with a zeolite-containing catalyst; and there are many reports relating to methods for producing ethylene and propylene through catalytic conversion from an olefin-containing hydrocarbon material with a zeolite-containing catalyst.

However, efficient, stable and long-lasting production of ethylene and propylene through catalytic conversion from an olefin-containing hydrocarbon material with a zeolite-containing catalyst was difficult for the following reasons.

Ethylene and propylene are intermediates in conversion from olefins to aromatic hydrocarbons in the presence of a zeolite catalyst, and they are converted into aromatic hydrocarbons through successive reaction. Accordingly, in case where ethylene and propylene are produced through catalytic conversion from an olefin-containing hydrocarbon material with a zeolite-containing catalyst, the activity of the catalyst and the reaction condition must be severely controlled for obtaining the product at high yield. Specifically, when the catalyst activity is too high or when the contact time is too long, then the produced ethylene and propylene would be converted into aromatic hydrocarbons through successive reaction. On the contrary, when the catalyst activity is too low or when the contact time is too short, then the yield of ethylene and propylene would be low.

On the other hand, olefins are highly reactive, and when an olefin-containing hydrocarbon material is subjected to catalytic conversion with a zeolite-containing catalyst, then a carbonaceous deposit may readily form on the surface of the catalyst (coking). Accordingly, during continuous conversion reaction, the catalyst may be degraded by coking (coking degradation), and the catalyst activity may soon lower.

The catalyst of which the catalytic activity has been lowered by coking degradation may be restored to its original catalytic activity generally by heating it in the presence of an oxygen-containing gas to thereby burn away the coke. However, when the regeneration operation is repeated, then the catalytic activity could not be sufficiently recovered. This is because, in the above regeneration operation, steam is formed through the coke combustion, and when zeolite is heated in the presence of the steam, then aluminium that is an active point of zeolite is released from zeolite crystals and the catalyst thereby undergoes permanent degradation (regeneration degradation).

As in the above, especially coking may often occur in catalytic conversion from an olefin-containing hydrocarbon material with a zeolite-containing catalyst, and therefore frequent regeneration of the catalyst is necessary and regeneration degradation of the catalyst may occur very often.

Patent Document 1 discloses a method of converting a paraffin, an olefin and/or a cycloparaffin (naphthene) having at least 5 carbon atoms into an aromatic hydrocarbon, ethylene and propylene with a proton-type ZSM-5 catalyst. In the method, however, the aromatic hydrocarbon may be obtained at relatively high yield but the yield of ethylene and propylene is low.

Patent Document 2 discloses a method of converting an olefin and a paraffin having from 2 to 4 carbon atoms into an aromatic hydrocarbon, ethylene and propylene with a proton-type ZSM-5 catalyst. Also in the method, the aromatic hydrocarbon may be obtained at relatively high yield but the yield of ethylene and propylene is low.

Patent Documents 3 and 4 disclose a method of converting butene into ethylene and propylene with an aluminophosphate-type molecular sieve. Also in this method, however, the yield of ethylene and propylene is low.

Patent Document 5 discloses a method of producing ethylene and propylene by contacting a hydrocarbon material of a mixture of a paraffin and an olefin having at least 4 carbon atoms and having a specific composition, with a proton-type ZSM5 zeolite. In this method, however, since the degree of conversion is low, a large amount of the unreacted material must be recycled.

Patent Document 6 discloses a method of converting a hydrocarbon having from 3 to 20 carbon atoms into ethylene and propylene with a phosphorus-containing, specific proton-type ZSM5 zeolite. In this method, however, where an olefin is used as the starting material, only the initial performance in 1 minute after the material supply is confirmed.

The characteristic common to the above methods is that a proton-type zeolite is used. In general, the proton-type zeolite has a high acid strength, with which, therefore, ethylene and propylene may be readily successively converted into an aromatic hydrocarbon, and the yield of ethylene and propylene is difficult to increase. In addition, when an olefin-containing hydrocarbon material is used, it often causes coking degradation and regeneration degradation.

Patent Document 7 discloses a proton-free zeolite catalyst that differs from conventional proton-containing zeolite catalysts, and discloses a method of using the catalyst for converting a hydrocarbon material into ethylene, propylene and a monocyclic aromatic hydrocarbon.

The catalyst used in this method is effective in that it hardly undergoes regeneration degradation, but could not still solve the problem of coking degradation. Accordingly, when a hydrocarbon material that contains a large amount of an olefin is processed, then it often causes coking degradation.

Patent Document 8 discloses a method of converting an olefin having from 4 to 12 carbon atoms into ethylene and propylene, with a IB Group metal-containing, aprotic intermediate pore-size zeolite that has a silica/alumina molar ratio of from 200 to 5000. However, the patent document says nothing about a significant influence of a shaped catalyst on the catalytic performance depending on the catalyst shaping method and about a negative influence thereof on the catalyst strength depending on the catalyst shaping method.

[Patent Document 1] JP-A-49-41322
[Patent Document 2] JP-A-50-49233
[Patent Document 3] U.S. Pat. No. 4,527,001
[Patent Document 4] U.S. Pat. No. 4,613,721
[Patent Document 5] JP-A-3-27327
[Patent Document 6] JP-A-6-73382

[Patent Document 7] WO1996/013331
[Patent Document 8] WO2000/010948

DISCLOSURE OF THE INVENTION

Problems that the Invention is to Solve

The invention relates to a method for producing ethylene and propylene through catalytic conversion from a hydrocarbon material, more precisely, to a method for producing ethylene and propylene through catalytic conversion from a hydrocarbon material, which comprises contacting a hydrocarbon material that contains at least one olefin having from 4 to 12 carbon atoms in an amount of at least 20% by weight, with a zeolite-containing shaped catalyst in a fixed-bed reactor to thereby produce ethylene and propylene through catalytic conversion of the at least one olefin having from 4 to 12 carbon atoms.

In the technique heretofore proposed, when a proton-type zeolite is used as a catalyst, then ethylene and propylene are readily successively converted into an aromatic hydrocarbon since the catalyst generally has a high acid strength, and therefore it is difficult to improve the yield of ethylene and propylene. In addition, when an olefin-containing hydrocarbon material is used, then it may cause another problem in that coking degradation and regeneration degradation may readily occur.

One example of using an aprotic zeolite proposed recently is Patent Document 8. However, Patent Document 8 says nothing at all about the strength of a zeolite-containing shaped catalyst that is important when catalytic conversion is carried out in a simple adiabatic fixed-bed reactor. This discloses in detail the activity and the degradation resistance of zeolite itself, but says nothing as to whether zeolite, after shaped, could still keep its properties.

The present inventors' studies revealed that, when the strength of a zeolite-containing shaped catalyst is low, then it may cause some problems in that it may form powder when filled in a fixed-bed reactor and that it may be cracked during its regeneration, therefore also forming powder. The catalyst powdering, if any, may cause some problems in that the reactor pressure loss may increase and the running maintenance would be thereby difficult, and that the reaction result may fluctuate owing to channeling.

On the other hand, however, when a zeolite-containing catalyst is shaped too tightly, then the catalyst may have some problems in that the diffusion into the zeolite pores thereof would be retarded and therefore the reaction activity thereof may lower and the coking degradation resistance thereof may also lower. Accordingly, when the invention is industrially carried out, a method of producing a zeolite-containing shaped catalyst is desired, in which time-dependent powdering of the catalyst is prevented and the properties of the starting zeolite are not worsened.

Means for Solving the Problems

Given that situation, the present inventors extensively studied for the purpose of solving the above problems and, as a result, found that when silica is used as a binder in shaping zeolite, when the side-crush strength of the zeolite-containing shaped catalyst is not lower than a predetermined level, and when the sodium concentration in the zeolite-containing shaped catalyst as an H-exchange type thereof is not higher than a predetermined level, then the troubles in powdering of the zeolite-containing shaped catalyst may be evaded without detracting from the intrinsic properties of the zeolite catalyst even though the method of the invention is industrially carried out in a simple adiabatic fixed-bed reactor; and as a result, we found that ethylene and propylene can be produced stably and efficiently for a long period of time in a simple manner, and have completed the present invention.

Specifically, the invention is a method for producing ethylene and propylene, as described below.

[1] A method for producing ethylene and propylene by contacting a hydrocarbon material that contains at least one olefin having from 4 to 12 carbon atoms in an amount of at least 20% by weight, with a zeolite-containing shaped catalyst in a fixed-bed reactor, to thereby carry out catalytic conversion of the at least one olefin having from 4 to 12 carbon atoms, wherein the zeolite-containing shaped catalyst satisfies the following requirements (1) to (6):

(1) the zeolite is an intermediate pore-size zeolite having a pore size of from 5 to 6.5 angstroms, (2) the zeolite does not substantially contain a proton, (3) the zeolite contains at least one metal selected from the group consisting of metals belonging to the Group IB of the Periodic Table, (4) the zeolite-containing shaped catalyst comprises silica as a binder, (5) the zeolite-containing shaped catalyst has a side-crush strength of at least 2.5 N/mm, (6) the zeolite-containing shaped catalyst has a sodium content of 500 ppm or less as an H-exchange type thereof.

[2] The method for producing ethylene and propylene of above [1], wherein the hydrocarbon material contains at least one olefin having from 4 to 12 carbon atoms in an amount of at least 50% by weight relative to the weight of the hydrocarbon material.

[3] The method for producing ethylene and propylene of above [1] or [2], wherein zeolite in the zeolite-containing shaped catalyst supports silver and an alkali metal through ion exchange, and does not substantially contain a proton.

[4] The method for producing ethylene and propylene of above [1] to [3], wherein zeolite in the zeolite-containing shaped catalyst is selected from the group consisting of ZSM-5-type zeolites.

[5] The method for producing ethylene and propylene of above [1] to [4], wherein zeolite in the zeolite-containing shaped catalyst has a silica/alumina molar ratio of from 800 to 2,000.

[6] The method for producing ethylene and propylene of above [1] to [5], wherein silica sol having a particle size of from 5 to 40 nm is used as a silica binder source in forming the zeolite-containing shaped catalyst.

[7] The method for producing ethylene and propylene of above [1] to [6], wherein the zeolite-containing shaped catalyst is heat-treated at a temperature not lower than 500° C. in the presence of water vapor, prior to its contact with the hydrocarbon material.

[8] The method for producing ethylene and propylene of above [1] to [7], wherein the fixed-bed reactor is an adiabatic fixed-bed reactor.

[9] The method for producing ethylene and propylene of above [1] to [8], wherein the catalytic conversion conditions are such that the reaction temperature is from 500 to 580° C., the hydrocarbon material partial pressure is from 0.05 to 0.3 MPa, and the weight-hourly space velocity is from 2 to 10 hr$^{-1}$.

Advantages of the Invention

With the zeolite-containing shaped catalyst of the invention, ethylene and propylene can be efficiently and stably produced from an olefin-based hydrocarbon material. The zeolite-containing shaped catalyst used in the method of the invention does not detract from the catalyst properties such as extremely high resistance to degradation, high activity and high selectivity that the zeolite catalyst of the invention has. When filled in a fixed-bed reactor, the catalyst does not powder and is therefore free from trouble of channeling, and its running management is easy. These characteristics are extremely advantageous in industrially carrying out the invention.

BEST MODE FOR CARRYING OUT THE INVENTION

The invention is described in detail hereinunder.

In the method of the invention, a hydrocarbon material containing at least one olefin having from 4 to 12 carbon atoms in an amount of at least 20% by weight is used as the starting material to produce ethylene and propylene.

In the method of the invention, "hydrocarbon material" represents a starting material essentially containing at least one selected from the group consisting of hydrocarbons having from 1 to 12 carbon atoms, for example, normal paraffins, isoparaffins, olefins, cycloparaffins (naphthenes) and cycloparaffins having a side-chain alkyl group, having from 1 to 12 carbon atoms.

In the method of the invention, the hydrocarbon material contains at least one olefin having from 4 to 12 carbon atoms in an amount of at least 20% by weight relative to the weight of the hydrocarbon material.

The term "olefin" as the constitutive element in the method of the invention is meant to include cycloparaffins in addition to linear, branched and cyclic olefins.

When the olefin content is less than 20% by weight, then the yield of ethylene and propylene may be insufficient. Accordingly, in the invention, the hydrocarbon material contains at least one olefin having from 4 to 12 carbon atoms in an amount of at least 20% by weight, preferably at least 30% by weight, more preferably at least 40% by weight, most preferably at least 50% by weight.

The hydrocarbon material may contain a small amount of oxygen-containing compounds such as tertiary-butanol, methyl tertiary-butyl ether, methanol, as impurities.

Preferred examples of the hydrocarbon material usable in the method of the invention are as follows:

(1) C4 fraction and C5 fraction separated from the product obtained through thermal cracking of petroleum hydrocarbon such as naphtha; and fraction obtained through partial hydrogenation of diolefins in the C4 fraction and C5 fraction into olefins;
(2) Fraction obtained through partial or complete separation and removal of butadiene and isobutene from the C4 fraction;
(3) Fraction obtained through partial or complete separation and removal of isoprene and cyclopentadiene from the C5 fraction;
(4) C4 fraction and gasoline fraction separated from the product obtained through fluid catalytic cracking (FCC) of petroleum hydrocarbon such as reduced-pressure light oil; and
(5) C4 fraction and gasoline fraction separated from coker.

One or more of these may be used herein either singly or as combined.

In the method of the invention, the above-mentioned hydrocarbon material is contacted with a specific zeolite-containing shaped catalyst in a reactor to attain catalytic conversion of at least one olefin having from 4 to 12 carbon atoms containing in the hydrocarbon material, thereby obtaining a reaction mixture that contains ethylene and propylene, and ethylene and propylene are separated from the resulting reaction mixture.

In the method of the invention, an "intermediate pore-size zeolite" that has a pore size of from 5 to 6.5 angstroms is used as the zeolite in the zeolite-containing shaped catalyst.

The term "intermediate pore-size zeolite" is meant to indicate "zeolite of which the pore size is intermediate between the pore size of a small pore-size zeolite such as typically A-type zeolite, and the pore size of a large pore-size zeolite such as typically mordenite, or X-type or Y-type zeolite", and this has a 10-membered oxygen ring in the crystal structure thereof.

Examples of the intermediate pore-size zeolite are ZSM-5, ZSM-8, ZSM-11, ZSM-12, ZSM-21, ZSM-23, ZSM-35, ZSM-38. Of those, preferred are ZSM-5-type zeolites such as ZSM-5, ZSM-11, ZSM-8, as well as ZSM-38.

In addition, zeolites similar to ZSM-5 and ZSM-11, as described in P. A. Jacobs and J. A. Martens, *Stud. Surf. Sci. Catal.*, 33, pp. 167-215 (1987, Holland) are also usable herein.

Of those, ZSM-5 is especially preferred.

The zeolite in the zeolite-containing shaped catalyst for use in the method of the invention is one substantially not containing a proton.

"Substantially not containing a proton" as referred to herein for the method of the invention means that the proton amount (acid amount) in the zeolite, as determined according to a liquid-phase ion exchange/filtrate titration method to be mentioned hereinunder, is 0.02 mmol or less per gram of the zeolite. Preferably, the proton amount in the zeolite is 0.01 mmol or less per gram of the zeolite.

The liquid-phase ion exchange/filtrate titration method is described in *Intrazeolite Chemistry*, "ACS Symp. Ser.", 218, pp. 369-382 (1983, USA); *Journal of the Chemical Society of Japan*, [3], pp. 521-527 (1989).

According to the method, the proton amount in the invention may be determined as follows:

A zeolite-containing shaped catalyst fired in air is ion-exchanged with an aqueous NaCl solution, and then the zeolite is recovered through filtration and the filtrate is obtained. The recovered zeolite is washed with pure water, and the resulting wash is entirely recovered and combined with the above filtrate. The proton amount in the resulting mixture is obtained through neutralization titration, and this is converted into a unit value per the zeolite weight in the zeolite-containing shaped catalyst, and this value indicates the proton amount in the zeolite.

It is known that ammonium ion-type and polyvalent metal cation-type zeolite (e.g., rare earth metal cation-type zeolite) produces a proton through heat treatment.

Accordingly, prior to the determination of the proton amount according to the above method, the zeolite-containing shaped catalyst must be fired.

The zeolite in the zeolite-containing shaped catalyst for use in the method of the invention is one that contains at least one metal selected from the group consisting of metals belonging to the Group IB of the Periodic Table (hereinafter referred to as "IB Group metal"), or that is, copper, silver, gold. Preferably, the IB Group metal is copper, silver, more preferably silver.

"The Periodic Table" as referred to in the invention is one described in *CRC Handbook of Chemistry and Physics*, 75th edition [(David R. Lide, et al., published by CRC Press Inc. (1994-1995)], pp. 1-15.

The above "containing a IB Group metal" means that the zeolite contains a IB Group metal as its corresponding cation. However, the IB Group metal may also be in the zeolite in any other state than its cation, in addition to the cation-state metal thereof; and for example, the metal may be therein as its oxide.

One example of incorporating a IB Group metal into zeolite comprises processing a IB Group metal-free zeolite for ordinary ion-exchange treatment. When a IB Group metal is incorporated into zeolite through ion-exchange treatment, a salt of the IB Group metal must be used. The IB Group metal salt includes, for example, silver nitrate, silver acetate, silver sulfate, copper chloride, copper sulfate, copper nitrate, gold chloride.

The amount of the IB Group metal to be in the zeolite-containing shaped catalyst as the IB Group metal cation is not strictly defined, but since the silica/alumina molar ratio ($SiO_2/Al_2O_3$ molar ratio) of the zeolite for use in the invention is from 800 to 2,000 and since the metal is held through ion exchange, the IB Group metal content shall be naturally determined from the exchange capacity and the zeolite content of the zeolite-containing shaped catalyst, as will be described hereinunder. Accordingly, when the amount is expressed in terms of the degree of exchange with the IB Group metal cation relative to the zeolite exchange site and when the degree of exchange is low, then the activity is not sufficient. When the degree of exchange is increased, then the load to the ion exchange and preparation process may be large. In general, therefore, the amount may fall within a range of from 5% to 80%, preferably from 25% to 75%, more preferably from 30% to 70%.

The IB Group metal content of zeolite may be determined in any known method, for example, according to X-ray fluorometric analysis.

As so mentioned in the above, zeolite in the zeolite-containing shaped catalyst in the method of the invention is one not substantially containing a proton, and therefore the ion-exchange site remaining after the IB Group metal cation exchange therein is ion-exchanged with a cation of at least one metal selected from alkali metals and alkaline earth metals. Preferably, it is exchanged with a cation of at least one metal selected from alkali metals, more preferably it is exchanged with a cation of at least one metal selected from the group consisting of sodium and potassium.

Accordingly, the zeolite in the zeolite-containing shaped catalyst in the method of the invention shall contain both at least one metal selected from alkali metals and alkaline earth metals, and a IB Group metal.

For incorporating at least one metal selected from alkali metals and alkaline earth metals into zeolite, employable is a method of ion-exchange treatment to make the corresponding cation held by the zeolite.

The content of at least one metal selected from alkali metals and alkaline earth metals varies depending on the type of the metal, but since the metal is held through ion-exchange treatment, its content shall be naturally determined from the exchange capacity, the zeolite content of the zeolite-containing shaped catalyst and the IB Group metal amount held through ion exchange.

When the zeolite-containing shaped catalyst of the invention is prepared, the order and the frequency of the process of incorporating at least one metal selected from alkali metals and alkaline earth metals into zeolite and the process of incorporating a IB Group metal thereinto are not specifically defined. In any case, however, it is necessary that the metal-incorporated zeolite should not substantially contain a protein, as so mentioned in the above.

For example, in case where the zeolite-containing shaped catalyst of the invention to be prepared is a silver/sodium cation exchange-type one, then a part of silver could not be held as a silver cation when an alkali component exists in the zeolite-containing shaped catalyst; and therefore, the zeolite must be converted into a proton-type one before it is shaped. Accordingly, one preferred method for it is as follows: The zeolite-containing shaped catalyst in which the shaped zeolite is a proton-type zeolite is first converted into a sodium-type one (preferably using an aqueous sodium nitrate solution), and the catalyst is thus converted into a sodium-type one (aprotic one), and thereafter a silver cation is introduced thereinto through ion exchange treatment (preferably using an aqueous silver nitrate solution).

The silica/alumina molar ratio ($SiO_2/Al_2O_3$ molar ratio) in the zeolite in the zeolite-containing shaped catalyst in the method of the invention is preferably from 800 to 2,000.

When the silica/alumina molar ratio is less than 800, then it is unfavorable since the degradation of the zeolite-containing shaped catalyst may be promoted owing to coking after conversion.

On the other hand, when the silica/alumina molar ratio is more than 2,000, then the problem in catalyst preparation may be great. In order to keep a high catalytic activity of the zeolite-containing shaped catalyst having such a high silica/alumina ratio and in order to prepare the catalyst having a silver content of the same level, the ion-exchange ratio of zeolite must be increased. However, when the zeolite-containing shaped catalyst of the invention is converted into an aprotic, IB Group metal-exchanged one through ion-exchange treatment, then the ion-exchange efficiency lowers with the increase in the ion-exchange ratio. Accordingly, zeolite having a silica/alumina molar ratio of more than 2,000 is unfavorable in the invention.

The silica/alumina molar ratio of the zeolite in the zeolite-containing shaped catalyst of the invention is preferably from 900 to 1,800, more preferably from 1,000 to 1,600.

The silica/alumina molar ratio of zeolite may be determined in a known method, for example, by completely dissolving zeolite in an aqueous alkali solution or an aqueous fluoric acid solution, then analyzing the resulting solution through plasma emission spectrometry.

As the zeolite in the zeolite-containing shaped catalyst in the method of the invention, also usable are metalloaluminosilicate in which the aluminium atom constituting the zeolite skeleton is partly substituted with an element of Ga, Fe, B, Cr; and metallosilicate in which the aluminium atom constituting the zeolite skeleton is completely substituted with the above-mentioned element.

In this case, the substituted element content of the metalloaluminosilicate or the metallosilicate is converted into the molar number of alumina, and then the silica/alumina molar ratio of the zeolite is computed.

If desired, the zeolite-containing shaped catalyst in the method of the invention may additionally contain at least one metal selected from the group consisting of metals belonging to Groups IIb, III, Vb, VIb, VIIb, VIII, such as V, Cr, Mo, W, Mn, Pt, Pd, Fe, Ni, Zn, Ga, for the purpose of prevention of coking degradation and for increasing the yield of ethylene and propylene.

The zeolite-containing shaped catalyst in the method of the invention may be heat-treated at a temperature not lower than 500° C. in the presence of water vapor before it is contacted with a hydrocarbon material, for the purpose of further improving its resistance to coking degradation. The heat treatment condition is preferably such that the temperature is from 500° C. to 900° C. and the water vapor partial pressure is at least 0.01 atmospheres.

The zeolite-containing shaped catalyst in the method of the invention may undergo coking degradation when used for conversion for a long period of time, but in such a case, in general, the coke on the catalyst may be burnt away in air or in a mixed gas of oxygen and an inert gas, at a temperature of from 400 to 700° C., whereby the catalyst having underwent coking degradation may be regenerated (hereinafter this treatment may be referred to as "regeneration").

The zeolite-containing shaped catalyst in the method of the invention may be produced by mixing zeolite with silica that serves as a binder or a shaping diluent (matrix), and shaping the resulting mixture, and the thus-obtained, shaped product is used as the zeolite-containing shaped catalyst. For shaping the catalyst, employable are a compression shaping method, and an extrusion shaping method, but preferred is an extrusion shaping method. Specifically, zeolite is mixed and kneaded with a binder source, silica sol, and shaped through extrusion with controlling the water content of the resulting cake, and then dried and fired to obtain a zeolite-containing extrusion-shaped catalyst.

The particle size of the silica sol to be used as the silica binder source in forming the zeolite-containing shaped catalyst for use in the method of the invention may depend on the balance between the stability of the silica sol and the strength of the shaped catalyst, but may be generally from 5 to 40 nm, preferably from 7 to 30 nm, more preferably from 10 to 20 nm.

The silica binder for the zeolite-containing shaped catalyst for use in the method of the invention is inert to the catalyst and has no influence on the catalyst performance. As opposed to this, when alumina or silica/alumina that is generally used as a catalyst binder is used in the invention in place of the silica binder, then the binder is not inert to the catalyst and may promote coking degradation with the result that the catalyst may lose the extremely high coking-resistant capability intrinsic to the zeolite catalyst.

The diameter of the zeolite-containing shaped catalyst in the method of the invention depends on the balance between the catalyst strength and the pressure loss in filling with the catalyst. Preferably, when it is an extrusion-shaped catalyst, its diameter may be from 1.5 mm to 5 mm. Not specifically defined, the length of the shaped catalyst may be preferably from 3 mm to 15 mm.

The amount of silica that is used as the matrix or binder in the zeolite-containing shaped catalyst for use in the method of the invention may be preferably from 10 to 90% by weight, more preferably from 20 to 50% by weight relative to the total weight of zeolite and the matrix or binder.

The zeolite-containing shaped catalyst for use in the method of the invention is previously processed into an H-exchange type one, after shaped, as so mentioned in the above. The zeolite-containing shaped catalyst in the method of the invention has a sodium concentration of 500 ppm or less as an H-exchange type thereof, preferably 400 ppm or less, more preferably 200 ppm or less. Sodium in the ion-exchange site in zeolite may be almost completely removed through ion exchange for H-exchanging treatment. Accordingly, sodium in the catalyst as referred to herein means the sum total of sodium contained in the silica sol added to the catalyst as a binder and sodium remaining in the zeolite exchange site not subjected to ion exchange therein.

Though not clear, the reason why the sodium amount may have some influence on the catalyst performance would be because sodium may promote the sintering (aggregation, coagulation) of silica serving as a binder, therefore forming a strong network with the result that the catalyst strength is thereby increased, but on the other hand, it would interfere with diffusion into zeolite pores, therefore causing the reduction in the catalytic activity and the reduction in the coking degradation resistance of the catalyst.

The zeolite-containing shaped catalyst in the method of the invention has a side-crush strength of at least 2.5 N/mm, preferably at least 4 N/mm, more preferably at least 6 N/mm.

The catalyst side-crush strength in the invention is represented by a value (N/mm) computed by dividing a found value (N) of the pressure under which a shaped catalyst sample set in a cross direction is pressed and crushed with a pressure pin having a pressure surface diameter of 3 mm, as measured with a hardness meter (Kiya-type hardness meter), by the pressure surface diameter (3 mm). The side-crush strength varies depending on the water content of the zeolite-containing shaped catalyst. Accordingly, the side-crush strength as referred to in the invention is one obtained by drying the zeolite-containing shaped catalyst at 120° C. for 3 hours or more and measuring the side-crush strength thereof in the manner as above.

The zeolite-containing shaped catalyst in the method of the invention has a side-crush strength of at least 2.5 N/m, and therefore, for example, even when it is used as filled in an adiabatic fixed-bed reactor and even when it is subjected to frequent reaction/regeneration, the catalyst is hardly cracked and is hardly powdered, and long-term safe operation with it is possible.

For making the zeolite-containing shaped catalyst in the method of the invention have the necessary side-crush strength as in the invention, it is needless-to-say important to control the shaping method, for example, by controlling the water content in extrusion shaping, but the strength significantly relies on the physical properties of the silica sol used herein as a binder source. The alkali ingredient (sodium) in the silica sol may be effective for expression of the catalyst strength, but as previously mentioned, the existence of sodium in the catalyst has some influence on the catalyst performance and therefore it is unfavorable to the method of the invention. Preferably, the particle size of the silica sol used as the binder in shaping is specifically defined, as so mentioned in the above. In the method of the invention, when a silica sol having a particle size of from 5 to 40 nm, then the catalyst strength may be increased.

In the method of the invention, the above zeolite-containing shaped catalyst is filled in a reactor, in which at least one olefin having from 4 to 12 carbon atoms is subjected to catalytic conversion. The catalytic conversion of an olefin having from 4 to 12 carbon atoms is preferably attained under the following condition under which the olefin having from 4 to 12 carbon atoms in the starting hydrocarbon material is converted into ethylene and propylene at high selectivity and the paraffin coexisting in the starting hydrocarbon material does not substantially participate in the reaction. The reaction temperature is preferably from 400 to 600° C., more preferably from 500 to 580° C. The partial pressure of the starting hydrocarbon material is preferably lower, generally from 0.01 to 1 MPa, preferably from 0.05 to 0.3 MPa. The weight hourly space velocity, WHSV, of the hydrocarbon material relative to the weight of the zeolite-containing shaped catalyst is preferably from 1 to 100 hr$^{-1}$, more preferably from 2 to 10 hr$^{-1}$. The contact time between the hydrocarbon material and the zeolite-containing catalyst is preferably 5 seconds or shorter, more preferably 1 second or shorter.

The starting hydrocarbon material may be a mixture with a diluent gas. The diluent gas may be an inert gas such as hydrogen, methane, water vapor, nitrogen. Preferably, however, the material does not undergo hydrogen dilution. Specifically, hydrogen may be used for preventing coking degradation of the catalyst, but at the same time it may have some negative influence in that it may hydrogenate the produced propylene to lower the propylene purity (propylene/(propylene+propane)). In the method of the invention, the coking degradation of the catalyst is low and stable operation is possible even though the material is not diluted with hydrogen, and therefore, it is desirable that the material is not diluted with hydrogen.

When the conversion is effected under the condition under which the paraffin does not substantially participate in the reaction, then the olefin conversion in the starting hydrocarbon material is selectively promoted while the paraffin conversion is inhibited with the result that the side production of methane, ethane and propane through paraffin conversion may be prevented, and therefore separation and purification of ethylene and propylene from the reaction mixture may be easy.

In the method of the invention, the reactor in which a starting hydrocarbon material is contacted with the zeolite-containing shaped catalyst is a fixed-bed reactor.

The zeolite-containing shaped catalyst for use in the method of the invention hardly undergoes coking degradation, and therefore, even though a fixed-bed reactor is used with it, ethylene and propylene may be stably produced therein for a long period of time. Paraffin conversion is great endothermic reaction, but olefin conversion is slight endothermic reaction or exothermic reaction though varying depending on the reaction condition. Accordingly, when the olefin in the starting hydrocarbon material is selectively reacted under the condition under which the above paraffin does not substantially participate in the reaction, then it is unnecessary to supply reaction heat to the system and therefore a single-stage, adiabatic fixed-bed reactor having a simple structure may be used.

EXAMPLES

The invention is described more concretely with reference to the following Examples and Comparative Examples, to which, however, the invention should not be limited.

The samples in Examples and Comparative Examples are analyzed as follows:

(1) Proton Determination through Liquid-Phase Ion-Exchange/Filtrate Titration:

2.5 g of a zeolite-containing shaped catalyst that had been ground in a mortar and burnt in air at a temperature of from 400 to 600° C. is ion-exchanged in 25 ml of an aqueous NaCl solution (3.4 mol/liter) with cooling with ice for 10 minutes. The resulting mixture is filtered, the zeolite is washed with 50 ml of pure water, and all the filtrate including the water used for washing is recovered. The filtrate (including the water used for washing) is neutralized through titration with an aqueous 0.1 N NaOH solution, and the proton amount is obtained from the neutralization point; and from the zeolite content of the zeolite-containing shaped catalyst, the thus-obtained value is converted into a zeolite weight-based proton amount in the sample.

(2) Determination of Silica/Alumina Ratio in Zeolite:

0.2 g of zeolite is added to 50 g of an aqueous 5 N NaOH solution. This is transferred into a stainless microcylinder equipped with a Teflon® inner tube, and the microcylinder is sealed up. This is kept in an oil bath for 15 to 70 hours to completely dissolve the zeolite. The resulting zeolite solution is diluted with ion-exchanged water, and the silicon and aluminium concentration in the diluted liquid is determined with a plasma emission spectrometer (ICP device). From the data, the silica/alumina molar ratio in the zeolite is computed.

ICP Device, and Measurement Condition:
Device: JOBIN YVON (JY138 ULTRACE) by Rigaku Denki Measurement Condition:
Silicon Measurement Wavelength: 251.60 nm
Aluminium Measurement Wavelength: 396.152 nm
Plasma Power: 1.0 kW
Nebulizer Gas: 0.28 L/min
Sheath Gas: 0.3 to 0.8 L/min
Coolant Gas: 13 L/min (3) Determination of Sodium Amount in H-type Zeolite-Containing Shaped Catalyst:

0.2 g of a ground, H-exchange-type, zeolite-containing shaped catalyst sample is weighed in a Teflon® container, and 6 ml of nitric acid (68% ultra-high-purity product) and 1 ml of fluoric acid (ultra-high-purity product) are added thereto, in which the sample is decomposed and dissolved under the condition of a decomposition temperature of 180° C. and a microwave power of 1000 W for a processing period of time of 50 minutes, using a microwave sample pretreatment device (ETHOS PLUS by Milestone General).

After thus dissolved, the obtained, zeolite-containing shaped catalyst solution is diluted with ion-exchanged water added thereto to be 20 g, and the sodium concentration in the diluted liquid is measured with a plasma emission spectrophotometer (ICP device), from which the sodium concentration in the zeolite-containing shaped catalyst is computed.

(4) Side-Crush Strength of Zeolite-Containing Shaped Catalyst:

A zeolite-containing shaped catalyst sample is previously dried at 120° C. for 3 hours or more. Using an automatic Kiya-type hardness meter (by Fujiwara Seisakusho) equipped with a pin having a pressure surface diameter of 3 mm, the pressure is measured under which the shaped catalyst sample set in a cross direction is crushed. The found value (N) is divided by the pressure surface diameter (3 mm) to give the side-crush strength (N/mm) of the sample.

(5) Degree of Conversion, Yield:

A degree of conversion (butene-based olefin conversion) is computed according to the following formula:

Degree of Conversion=(C4 to C8 olefin concentration in starting material−butene concentration in product)/(C4 to C8 olefin concentration in starting material).

Ethylene and propylene yield is represented by the ethylene or propylene concentration (% by weight) in the product.

Example 1

An H-type ZSM5 zeolite having a silica/alumina molar ratio of 1068 (as measured through ICP by completely dissolving the zeolite-containing shaped catalyst) was mixed with Nissan Chemical Industries' colloidal silica, Snowtex ST-N (catalogue data: $SiO_2$ concentration, 20% by weight; particle size, 10 to 20 nm; $Na_2O$ content, 0.04% by weight or less), its water content was controlled, and this was extruded and shaped. The resulting shaped article was dried at 120° C. for 6 hours and then fired at 550° C. for 6 hours to obtain a zeolite-containing shaped catalyst (containing 30% by weight of $SiO_2$ binder, 1.6 mmφ×5 to 10 mmL). The obtained, zeolite-containing shaped catalyst was dispersed in an aqueous 1 N nitric acid solution (10 cc/g-shaped zeolite), and ion-exchanged at room temperature for 1 hour. Next, this was filtered, washed with water and dried to prepare an H-exchange-type ZSM-5/$SiO_2$ shaped catalyst.

The sodium concentration in the obtained, H-exchange-type ZSM-5/$SiO_2$ shaped catalyst was measured according to a fluoric acid dissolution method, and was 230 wt.ppm.

The obtained, H-exchange-type ZSM-5/$SiO_2$ shaped catalyst was dispersed in an aqueous 1 N sodium nitrate solution (10 cc/g-shaped zeolite), and subjected to one-hour ion-exchanging treatment repeatedly three times at room temperature. Next, this was filtered, washed with water and dried to prepare an Na-exchange-type ZSM-5/$SiO_2$ shaped catalyst. This was dispersed in an aqueous 0.00145 N silver nitrate solution (10 cc/g-shaped zeolite), and ion-exchanged for 2 hours at room temperature. Next, this was filtered, washed with water and dried to prepare a catalyst A.

The Ag amount in the catalyst A, as determined through X-ray fluorometric analysis, was 0.084% by weight. Specifically, the silver cation population (ion exchange ratio) relative to the zeolite exchange site (aluminium amount) was 36.6%.

On the other hand, the mean side-crush strength of 30 particles of the catalyst A, as measured with a Kiya-type hardness meter, was 6.3 N/mm.

The catalyst A was filled in a hastelloy C reactor having an inner diameter of 27.2 mmφ, and steamed for 5 hours under the condition of a temperature of 650° C., a steam flow rate of 218 g/hr, and a nitrogen flow rate of 220 NL/hr.

After steamed, the proton amount in the catalyst A was determined through liquid-phase ion-exchange/filtrate titration, and was 0.0015 mmol/g-zeolite.

60 g of the seamed catalyst A was filled in a hastelloy C reactor having an inner diameter of 27.2 mmφ and equipped with a 2-μm sintered SUS filter for powdered catalyst recovery at the outlet port of the reactor tube.

C4 raffinate-2 (obtained through steam cracking of naphtha followed by extraction of butadiene and isobutene from the resulting C4 fraction) as in Table 1 was used as the starting material. This was processed under the condition of a reaction temperature of 550° C., a C4 raffinate-2 supply rate of 435 g/hr (WHSV=7.25 $hr^{-1}$), and 0.1 MPaG.

The reaction product in a predetermined period of time after the start of the supply of the starting material was directly led into a gas chromatographic analyzer (TCD, FID detector) from the outlet port of the reactor, and analyzed for its composition.

The gas chromatographic analysis was under the following condition.

(Gas Chromatographic Analysis Condition),
  Device: Shimadzu's GC-17A,
  Column: US SUPELCO's custom capillary column SPB-1 (inner diameter 0.25 mm, length 60 m, film thickness 3.0 μm),
  Sample Gas Amount: 1 ml (sampling line was kept warmed at 200 to 300° C.),
  Heating Program: Kept at 40° C. for 12 minutes, then heated up to 200° C. at a rate of 5° C./min, and then kept at 200° C. for 22 minutes,
  Split Ratio: 200/1,
  Carrier Gas (nitrogen) Flow Rate: 120 ml/min,
  FID Detector: air supply pressure 50 kPa (about 500 ml/min), hydrogen supply pressure 60 kPa (about 50 ml/min),
  Measurement Method: TCT detector and FID detector are connected in series, and hydrogen and C1 and C2 hydrocarbons are detected with TCD detector, and hydrocarbons of C3 or more are detected with FID detector. 10 minutes after the start of the analysis, the detection output is switched from TCD to FID.

Suitably analyzing the reaction product, the reaction was continued for 48 hours. The results are shown in Table 2.

The propylene yield difference between 2 hours and 48 hours after the start of the reaction in this Example [PY yield (2 hours)—PY yield (48 hours)] was kept only 2.4%.

In 48 hours, the supply of the starting material was stopped, and for a while the catalyst layer was cooled to 480° C. while the system was purged with nitrogen. Then, 1% oxygen/99% nitrogen gas was fed at 16.8 NL/hr, and the coke having adhered to the catalyst was burnt away (for regeneration). While the outlet port gas was analyzed for the CO and $CO_2$ concentration therein, the firing temperature and the oxygen concentration were gradually increased, and finally, the catalyst was regenerated at an oxygen concentration of 5 vol.% and at a temperature of 580° C. for 12 hours.

After thus regenerated, the zeolite-containing shaped catalyst was again used for the reaction under the above condition for 48 hours. Similarly, this was subjected to 20 cycles of 48-hours reaction/12-hours regeneration each. The results are shown in Table 3. The catalyst performance (initial activity, coking degradation resistance) did not change. During 20 cycles, the pressure difference between the reactor tube inlet port and the outlet port did not change.

From this Example, it is known that, in the zeolite-containing shaped catalyst of the invention, the zeolite did not lose its catalytic performance, and the catalyst expressed high activity and extremely high resistance to coking degradation and to regeneration degradation, and that the catalyst did not powder in frequent reaction/regeneration cycle operation.

Comparative Example 1

An H-exchange-type, zeolite-containing shaped catalyst was prepared in the same manner as in Example 1, for which, however, Nissan Chemical Industries' colloidal silica, Snowtex ST30 (catalogue data: $SiO_2$ concentration, 30% by weight; particle size, 10 to 20 nm; $Na_2O$ content, 0.6% by weight or less) was used as the catalyst-shaping binder.

The sodium concentration in the obtained, H-exchange-type ZSM-5/$SiO_2$ shaped catalyst was measured according to a fluoric acid dissolution method, and was 2200 wt.ppm.

The obtained, H-exchange-type MM-5/$SiO_2$ shaped catalyst was dispersed in an aqueous 1 N sodium nitrate solution (10 cc/g-shaped zeolite), and subjected to one-hour ion-exchanging treatment repeatedly three times at room temperature. Next, this was filtered, washed with water and dried to prepare an Na-exchange-type ZSM-5/$SiO_2$ shaped catalyst. This was dispersed in an aqueous 0.00145 N silver nitrate solution (10 cc/g-shaped zeolite), and ion-exchanged for 2 hours at room temperature. Next, this was filtered, washed with water and dried to prepare a catalyst B.

The Ag amount in the catalyst B, as determined through X-ray fluorometric analysis, was 0.083% by weight. Specifically, the silver cation population (ion exchange ratio) relative to the zeolite exchange site (aluminium amount) was 35.4%.

On the other hand, the mean side-crush strength of 30 particles of the catalyst B, as measured with a Kiya-type hardness meter, was 7.5 N/mm.

The catalyst B was filled in a hastelloy C reactor having an inner diameter of 27.2 mmφ, and steamed for hours under the condition of a temperature of 650° C., a steam flow rate of 218 g/hr, and a nitrogen flow rate of 220 NL/hr.

After steamed, the proton amount in the catalyst A was determined through liquid-phase ion-exchange/filtrate titration, and was 0.0015 mmol/g-zeolite.

The steamed catalyst B was tested for the reaction with it, under the same condition as in Example 1. The reaction results are shown in Table 2.

The activity degradation was remarkable, and in 20 hours after the start of the reaction, the degree of conversion was lowered to 32%, and the test was stopped in this stage. The propylene yield difference between 2 hours and 20 hours was 9.5%.

From this Comparative Example, it is known that the zeolite-containing shaped catalyst of which the sodium content is more than 500 ppm, as defined as an H-type catalyst in the invention, may be a tough catalyst (having a high strength) owing to the sintered silica therein, but diffusion into the zeolite pores would be retarded and the coking degradation of the catalyst is remarkable, and therefore the catalyst significantly lost the degradation resistance intrinsic to zeolite.

Comparative Example 2

An H-exchange-type, shaped catalyst of ZSM-5/SiO$_2$ was prepared in the same manner as in Example 1, for which, however, Nissan Chemical Industries' colloidal silica, Snowtex ST-OL (catalogue data: SiO$_2$ concentration, 20% by weight; particle size, 40 to 50 nm; Na$_2$O content, 0.05% by weight or less) was used as the catalyst-shaping binder.

The sodium concentration in the obtained, H-exchange-type ZSM-5/SiO$_2$ shaped catalyst was measured according to a fluoric acid dissolution method, and was 330 wt.ppm.

The obtained, H-exchange-type ZSM-5/SiO$_2$ shaped catalyst was dispersed in an aqueous 1 N sodium nitrate solution (10 cc/g-shaped zeolite), and subjected to one-hour ion-exchanging treatment repeatedly three times at room temperature. Next, this was filtered, washed with water and dried to prepare an Na-exchange-type ZSM-5/SiO$_2$ shaped catalyst. This was dispersed in an aqueous 0.00145 N silver nitrate solution (10 cc/g-shaped zeolite), and ion-exchanged for 2 hours at room temperature. Next, this was filtered, washed with water and dried to prepare a catalyst C.

The Ag amount in the catalyst C, as determined through X-ray fluorometric analysis, was 0.085% by weight. Specifically, the silver cation population (ion exchange ratio) relative to the zeolite exchange site (aluminium amount) was 36.2%.

On the other hand, the mean side-crush strength of 20 particles of the catalyst C, as measured with a Kiya-type hardness meter, was 1.4 N/mm.

The catalyst C was filled in a hastelloy C reactor having an inner diameter of 27.2 mmφ, and steamed for 5 hours under the condition of a temperature of 650° C., a steam flow rate of 218 g/hr, and a nitrogen flow rate of 220 NL/hr.

After steamed, the proton amount in the catalyst C was determined through liquid-phase ion-exchange/filtrate titration, and was 0.0015 mmol/g-zeolite.

The steamed catalyst C was tested for the reaction with it, under the same condition as in Example 1. The reaction results are shown in Table 2.

The propylene yield difference between 2 hours and 48 hours after the start of the reaction in this Comparative Example was 2.7%, and was small.

In the same manner as in Example 1, the catalyst was subjected to the cycle test of 48-hours reaction/12-hours regeneration, in which the pressure difference at the reactor outlet port during nitrogen purging for regeneration in one cycle was 5 KPa. In 10 cycles, the pressure difference at the reactor outlet port during nitrogen purging for regeneration increased up to 35 KPa, and therefore the experiment was stopped in this stage. The results are shown in Table 3. The reactor pipe outlet port line filter was taken apart to pieces, in which a white powder was seen. The white powder was analyzed with an electronic microscope, and it was a fine powder of the zeolite-containing shaped catalyst.

From this Comparative Example, it is known that the sodium amount of the H-type zeolite-containing shaped catalyst, as defined in the invention, was 330 ppm and its catalytic performance is good, but its side-crush strength was 1.4 N/mm and is low. Therefore, while the zeolite-containing shaped catalyst was subjected to frequently-repeated reaction/regeneration in a fixed-bed reactor, it gave a fine powder.

TABLE 1

| C4 Raffinate-2 | |
| --- | --- |
| Ingredient | Composition Ratio (wt. %) |
| Methylacetylene | 0.00 |
| Propadiene | 0.15 |
| Propylene | 0.12 |
| Propane | 0.22 |
| Butadiene | 0.62 |
| Butene | 81.05 |
| Butane | 17.55 |
| Pentene | 0.08 |
| Pentane | 0.17 |
| Benzene | 0.00 |
| C6 Non-aromatic Hydrocarbon | 0.00 |
| Toluene | 0.00 |
| C7 Non-aromatic Hydrocarbon | 0.03 |
| C8 Aromatic Hydrocarbon | 0.00 |
| C8 Non-aromatic Hydrocarbon | 0.00 |
| C9+ Hydrocarbon | 0.00 |
| Total | 100.00 |

TABLE 2

| | | | | | | |
| --- | --- | --- | --- | --- | --- | --- |
| Example 1 (Catalyst A) | Silica/Alumina Molar Ratio | 1068 | | | | |
| | Silver Content (wt. %) | 0.086 | | | | |
| | Starting Material | C4 Raffinate-2 | | | | |
| | Reaction Time | 2 | 20 | 38 | 48 | |
| | C4 Olefin Conversion (wt. %) | 67.97 | 64.46 | 60.41 | 60.01 | |
| | Ethylene Yield (wt. %) | 4.95 | 3.83 | 3.11 | 3.07 | |
| | Propylene Yield (wt. %) | 23.71 | 22.97 | 21.56 | 21.34 | |
| Comparative Example 1 (Catalyst B) | Silica/Alumina Molar Ratio | 1068 | | | | |
| | Silver Content (wt. %) | 0.083 | | | | |
| | Starting Material | C4 Raffinate-2 | | | | |
| | Reaction Time | 2 | 8 | 14 | 20 | |
| | C4 Olefin Conversion (wt. %) | 57.74 | 43.68 | 35.41 | 31.63 | |
| | Ethylene Yield (wt. %) | 2.79 | 1.27 | 0.83 | 0.69 | |
| | Propylene Yield (wt. %) | 19.44 | 14.34 | 11.35 | 9.97 | |

TABLE 2-continued

| | | | | | |
|---|---|---|---|---|---|
| Comparative Example 2 (Catalyst C) | Silica/Alumina Molar Ratio | 1068 | | | |
| | Silver Content (wt. %) | 0.085 | | | |
| | Starting Material | C4 Raffinate-2 | | | |
| | Reaction Time | 2 | 20 | 38 | 48 |
| | C4 Olefin Conversion (wt. %) | 67.47 | 63.87 | 62.02 | 59.06 |
| | Ethylene Yield (wt. %) | 4.65 | 3.50 | 3.44 | 3.00 |
| | Propylene Yield (wt. %) | 23.56 | 22.65 | 22.05 | 20.90 |

C4 Olefin Conversion (wt. %) = (C4-8 olefin concentration in starting material − butene concentration in product)/(C4-8 olefin concentration in starting material).
Ethylene, Propylene Yield (wt. %): ethylene, propylene concentration in product.

TABLE 3

| | | Cycle No. | | | | | |
|---|---|---|---|---|---|---|---|
| | | 1 | 2 | 5 | 10 | 15 | 20 |
| Example 1 (Catalyst A) | C4 Olefin Conversion (2 hrs) | 67.97 | 68.00 | 67.39 | 67.00 | 67.21 | 67.27 |
| | Propylene Yield (2 hrs) | 23.72 | 23.42 | 23.41 | 23.28 | 23.11 | 23.18 |
| | Propylene Yield (48 hrs) | 21.34 | 21.19 | 21.31 | 21.03 | 21.17 | 20.70 |
| | Inlet/Outlet Port in Regeneration ΔP (KPa) | 2 | 2 | 1 | 2 | 2 | 2 |

| | | Cycle No. | | |
|---|---|---|---|---|
| | | 1 | 5 | 10 |
| Comparative Example 2 (Catalyst B) | C4 Olefin Conversion (2 hrs) | 67.47 | 66.95 | 67.15 |
| | Propylene Yield (2 hrs) | 23.56 | 23.30 | 23.22 |
| | Propylene Yield (48 hrs) | 20.90 | 20.67 | 20.52 |
| | Inlet/Outlet Port in Regeneration ΔP (KPa) | 5 | 15 | 35 |

C4 Olefin Conversion (wt. %) = (C4-8 olefin concentration in starting material − butene concentration in product)/(C4-8 olefin concentration in starting material).
Propylene Yield (wt. %): propylene concentration in product.

INDUSTRIAL APPLICABILITY

The invention has been described in detail and with reference to its specific embodiments, and it is obvious to anyone skilled in the art that various changes and modifications may be added thereto not overstepping the sprit and the scope of the invention.

This application is based on Japanese Patent Application Nos. 2005-270323 (filed Sep. 16, 2005) and 2005-360229 (filed Dec. 14, 2005), the entire contents thereof being herein incorporated by reference.

In a method for producing ethylene and propylene through catalytic conversion from a hydrocarbon material, in which a hydrocarbon material that contains at least one olefin having from 4 to 12 carbon atoms in an amount of at least 20% by weight is contacted with a zeolite-containing shaped catalyst in a fixed-bed reactor to attain catalytic conversion of the at least one olefin having from 4 to 12 carbon atoms to produce ethylene and propylene, when the zeolite-containing shaped catalyst of the invention is used, then ethylene and propylene can be produced efficiently and stably. This is because, since the zeolite-containing shaped catalyst to be used in the method of the invention can be formed as an industrially-practicable shaped catalyst not detracting from its excellent catalytic performance intrinsic to original zeolite catalyst, it is extremely highly resistant to deterioration, and therefore the products can be stably produced at high yield for a long period of time in a simple manner. The zeolite-containing shaped catalyst of the invention is free from a trouble of powdering even in repeated cycle use for reaction/regeneration, and it may evade the powdering trouble in the running system maintenance.

These characteristics are extremely advantageous in industrially carrying out the invention.

The invention claimed is:

1. A method for producing ethylene and propylene by contacting a hydrocarbon material that contains at least one olefin having from 4 to 12 carbon atoms in an amount of at least 20% by weight, with a zeolite-containing shaped catalyst in a fixed-bed reactor, to thereby carry out catalytic conversion of the at least one olefin having from 4 to 12 carbon atoms, wherein the zeolite-containing shaped catalyst satisfies the following requirements (1) to (6):
    (1) the zeolite is an intermediate pore-size zeolite having a pore size of from 5 to 6.5 angstroms,
    (2) the zeolite does not substantially contain a proton,
    (3) the zeolite contains at least one metal selected from the group consisting of metals belonging to the Group IB of the Periodic Table,
    (4) the zeolite-containing shaped catalyst comprises silica as a binder,
    (5) the zeolite-containing shaped catalyst has a side-crush strength of at least 2.5 N/mm,
    (6) the zeolite-containing shaped catalyst has a sodium content of 500 ppm or less as an H-exchange type thereof.

2. The method for producing ethylene and propylene as claimed in claim 1, wherein the hydrocarbon material contains at least one olefin having from 4 to 12 carbon atoms in an amount of at least 50% by weight relative to the weight of the hydrocarbon material.

3. The method for producing ethylene and propylene as claimed in claim 1, wherein zeolite in the zeolite-containing shaped catalyst supports silver and an alkali metal through ion exchange, and does not substantially contain a proton.

4. The method for producing ethylene and propylene as claimed in claim 1, wherein zeolite in the zeolite-containing shaped catalyst is selected from the group consisting of ZSM-5, ZSM-8, ZSM-11, ZSM-12, ZSM-21, ZSM-23, ZSM-35 and ZSM-38 zeolites.

5. The method for producing ethylene and propylene as claimed in claim 1, wherein zeolite in the zeolite-containing shaped catalyst has a silica/alumina molar ratio of from 800 to 2,000.

6. The method for producing ethylene and propylene as claimed in claim 1, wherein silica sol having a particle size of from 5 to 40 nm is used as a silica binder source in forming the zeolite-containing shaped catalyst.

7. The method for producing ethylene and propylene as claimed in claim 1, wherein the zeolite-containing shaped catalyst is heat-treated at a temperature not lower than 500° C. in the presence of water vapor, prior to its contact with the hydrocarbon material.

8. The method for producing ethylene and propylene as claimed in claim 1, wherein the fixed-bed reactor is an adiabatic fixed-bed reactor.

9. The method for producing ethylene and propylene as claimed in claim 1, wherein the catalytic conversion conditions are such that the reaction temperature is from 500 to 580° C., the hydrocarbon material partial pressure is from 0.05 to 0.3 MPa, and the weight-hourly space velocity is from 2 to 10 hr$^{-1}$.

10. A method for producing ethylene and propylene as claimed in claim 1, wherein the catalytic conversion (reaction) is continued for 38 hours or more.

* * * * *